US010988600B2

(12) United States Patent
Edsman et al.

(10) Patent No.: US 10,988,600 B2
(45) Date of Patent: Apr. 27, 2021

(54) CYCLODEXTRIN-GRAFTED CROSS-LINKED HYALURONIC ACID COMPLEXED WITH ACTIVE DRUG SUBSTANCES AND USES THEREOF

(71) Applicant: GALDERMA S.A., Cham (CH)

(72) Inventors: Katarina Edsman, Alunda (SE); Jean-Guy Boiteau, Valbonne (FR)

(73) Assignee: GALDERMA HOLDING SA, La Tour-de-Peilz (CH)

( * ) Notice: Subject to any disclaimer, the term of this patent is extended or adjusted under 35 U.S.C. 154(b) by 0 days.

(21) Appl. No.: 16/312,079

(22) PCT Filed: Jun. 20, 2017

(86) PCT No.: PCT/EP2017/065152
§ 371 (c)(1),
(2) Date: Dec. 20, 2018

(87) PCT Pub. No.: WO2017/220622
PCT Pub. Date: Dec. 28, 2017

(65) Prior Publication Data
US 2019/0233620 A1     Aug. 1, 2019

(30) Foreign Application Priority Data
Jun. 23, 2016  (EP) .................................... 16175864

(51) Int. Cl.
| | |
|---|---|
| *C08L 5/08* | (2006.01) |
| *C08L 5/16* | (2006.01) |
| *A61K 9/16* | (2006.01) |
| *C08K 5/1515* | (2006.01) |
| *A61K 8/02* | (2006.01) |
| *A61Q 19/00* | (2006.01) |
| *C08J 3/075* | (2006.01) |
| *A61K 8/73* | (2006.01) |
| *C08B 37/16* | (2006.01) |
| *C08B 37/08* | (2006.01) |
| *A61K 47/36* | (2006.01) |
| *A61K 9/00* | (2006.01) |
| *A61K 9/06* | (2006.01) |
| *C08J 3/12* | (2006.01) |
| *A61K 31/216* | (2006.01) |

(52) U.S. Cl.
CPC .............. *C08L 5/08* (2013.01); *A61K 8/0283* (2013.01); *A61K 8/735* (2013.01); *A61K 9/0014* (2013.01); *A61K 9/06* (2013.01); *A61K 9/1694* (2013.01); *A61K 47/36* (2013.01); *A61Q 19/00* (2013.01); *C08B 37/0012* (2013.01); *C08B 37/0072* (2013.01); *C08J 3/075* (2013.01); *C08J 3/12* (2013.01); *C08K 5/1515* (2013.01); *C08L 5/16* (2013.01); *A61K 31/216* (2013.01); *C08J 2305/08* (2013.01); *C08J 2305/16* (2013.01); *C08J 2405/08* (2013.01); *C08J 2405/16* (2013.01); *C08L 2312/00* (2013.01)

(58) Field of Classification Search
None
See application file for complete search history.

(56) References Cited

U.S. PATENT DOCUMENTS

| | | | |
|---|---|---|---|
| 2004/0076680 | A1 | 4/2004 | Soltes et al. |
| 2005/0276841 | A1* | 12/2005 | Davis ................... A61K 9/0051 424/443 |
| 2008/0008727 | A1 | 1/2008 | Fredon et al. |
| 2012/0077970 | A1 | 3/2012 | Lochard et al. |
| 2012/0094954 | A1 | 4/2012 | At et al. |
| 2013/0123210 | A1 | 5/2013 | Liu et al. |
| 2014/0094433 | A1 | 4/2014 | Liu et al. |
| 2016/0279290 | A1 | 9/2016 | Liu et al. |
| 2017/0196991 | A1 | 7/2017 | Boiteau et al. |
| 2017/0210829 | A1 | 7/2017 | Boiteau |
| 2018/0265600 | A1 | 9/2018 | Boiteau et al. |

FOREIGN PATENT DOCUMENTS

| | | |
|---|---|---|
| JP | 3847405 B2 | 11/2006 |
| WO | 2013/040242 A2 | 3/2013 |
| WO | 2015/181365 A1 | 12/2015 |
| WO | 2015/181366 A1 | 12/2015 |

OTHER PUBLICATIONS

International Search Report (PCT/ISA/210) dated Oct. 13, 2017, by the European Patent Office as the International Searching Authority for International Application No. PCT/EP2017/065152.
Written Opinion (PCT/ISA/237) dated Oct. 13, 2017, by the European Patent Office as the International Searching Authority for International Application No. PCT/EP2017/065152.
Borke, T. et al., "Optimized triazine-mediated amidation for efficient and controlled functionalization of hyaluronic acidTina", Carbohydrate Polymers, 116, pp. 42-50, 2015.
Carruthers, A. et al., "Randomized, Double-Blind Comparison of the Efficacy of Two Hyaluronic Acid Derivatives, Restylane Perlane and Hylaform, in the Treatment of Nasolabial Folds", Dermatol Surg, 31:11, Part 2, pp. 1591-1598, Nov. 2005, XP55203648.

(Continued)

*Primary Examiner* — Patricia Duffy
*Assistant Examiner* — Garen Gotfredson
(74) *Attorney, Agent, or Firm* — Foley & Lardner LLP; Sunit Talapatra

(57) ABSTRACT

A hyaluronic acid product is comprising a cross-linked hyaluronic acid and one or more cyclodextrin molecules, and further comprising a guest molecule capable of forming a guest-host complex with the aminocyclodextrin molecule acting as a host, wherein the guest molecule is a retinoid, preferably adapalene, or a RAM BA. The hyaluronic acid is cross-linked by ether bonds, and the one or more cyclodextrin molecules are grafted onto the cross-linked hyaluronic acid by amide bonds, preferably using a triazine-based coupling reagent.

17 Claims, 4 Drawing Sheets

(56) References Cited

OTHER PUBLICATIONS

Charlot, A. et al., "Novel Hyaluronic Acid Based Supramolecular Assemblies Stabilized by Multivalent Specific Interactions: Rheological Behavior in Aqueous Solution", Macromolecules, vol. 40, No. 26, pp. 9555-9563, 2007, XP55203405.

D'Este, M. et al., "A systematic analysis of DMTMM vs EDC/NHS for ligation of amines to Hyaluronan in water", Carbohydrate Polymers, vol. 108, pp. 239-246, 2014.

Falcone, S.J. et al., "Crosslinked hyaluronic acid dermal fillers: of rheological properties a comparison of rheological properties", Journal of Biomedical Materials Research, Part A, pp. 264-271, 2008, XP55203615A.

Li, N. et al., "Polysaccharide-Gold Nanocluster Supra molecular Conjugates as a Versatile Platform for the Targeted Delivery of Anticancer Drugs", Scientific Reports, pp. 1-7, 2013-2014, XP55203406.

Rodell, C.B. et al., "Shear-Thinning Supramolecular Hydrogels with Secondary Autonomous Covalent Crosslinking to Modulate Viscoelastic Properties In Vivo", Adv. Funct. Mater., 25, pp. 636-644, 2015.

* cited by examiner

CYCLODEXTRIN-GRAFTED CROSS-LINKED HYALURONIC ACID COMPLEXED WITH ACTIVE DRUG SUBSTANCES AND USES THEREOF

TECHNICAL FIELD OF THE INVENTION

The present invention relates to the field of hydrogels containing cross-linked polysaccharides and the use of such hydrogels in medical and/or cosmetic applications. More specifically, the present invention deals with cross-linked hyaluronic acid hydrogels, functionalized with cyclodextrin which is complexed with active drug substances, preferably with retinoid substances or retinoic acid metabolism blocking agents (RAMBAs).

BACKGROUND TO THE INVENTION

One of the most widely used biocompatible polymers for medical use is hyaluronic acid (HA). It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical crosslinking of polymers to infinite networks. While native hyaluronic acid and certain crosslinked hyaluronic acid products absorb water until they are completely dissolved, crosslinked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of reactions and allows for advanced medical uses. Crosslinking and/or other modifications of the hyaluronic acid molecule is necessary to improve its duration in vivo. Furthermore, such modifications affect the liquid retention capacity of the hyaluronic acid molecule. As a consequence thereof, hyaluronic acid has been the subject of many modification attempts.

Cyclodextrins (sometimes called cycloamyloses), also referred to herein as CD or CDx, are a family of compounds made up of sugar molecules bound together in a ring (cyclic oligosaccharides). Cyclodextrins are produced from starch by means of enzymatic conversion. Typically, cyclodextrins are constituted by 6-8 glucopyranoside units, and have a structural conformation resembling toroids with the primary hydroxyl groups of the glucopyranoside units arranged along the smaller opening of the toroid and the secondary hydroxyl groups of the glucopyranoside units arranged along the larger opening of the toroid. Because of this arrangement, the interior of the toroids is considerably less hydrophilic than the aqueous environment and thus able to host other hydrophobic molecules. In contrast, the exterior is sufficiently hydrophilic to impart cyclodextrins (or their complexes) water solubility.

When a hydrophobic molecule (the guest) is contained, fully or partially, within the interior of the cyclodextrin (the host), this is referred to as an inclusion complex or guest/host complex. The formation of the guest/host complex can greatly modify the physical and chemical properties of the guest molecule, mostly in terms of water solubility. This is a reason why cyclodextrins have attracted much interest in pharmaceutical applications: because inclusion compounds of cyclodextrins with hydrophobic molecules are able to penetrate body tissues, these can be used to release biologically active compounds under specific conditions. In most cases the mechanism of controlled degradation of such complexes is based on change of pH, leading to the cleavage of hydrogen or ionic bonds between the host and the guest molecules. Other mechanisms for the disruption of the complexes include heating or action of enzymes able to cleave $\alpha$-1,4 linkages between glucose monomers.

WO 2013/040242 A2 discloses that additives containing carboxyl functional groups can be conjugated to hyaluronic acid hydrogels via esterifications using EDC chemistry. Example 14 of WO 2013/040242 provides however merely a prophetic example of conjugation of retinoic acid and non-crosslinked hyaluronic acid.

US 2014/0094433 discloses a one-step process of simultaneous cross-linking of HA and grafting of cyclodextrins. The grafting may occur either by direct covalent bonds, e.g. ester bonds, between HA and the cyclodextrin or by a linking group covalently bonded to both the HA and the cyclodextrin, e.g. by ester, ether, amine, amide or other covalent bonds.

JP 3847405 B2 is concerned with coupling of monosaccharides to cyclodextrins in the presence of an endoglucosidase, which enzymatically degrades oligosaccharides.

WO 2015/181365 A1 and WO 2015/181366 A1 discloses a hydrogel consisting of hyaluronic acid cross-linked by ether bonds to dextran, further comprising a cyclodextrin cross-linked by amide bonds to the hyaluronic acid moieties. The cyclodextrin moiety is comprising a drug substance.

Chariot et al., Macromolecules 40(26): 9555-9563 (2007) discloses a guest-host complex between adamantane coupled to hyaluronic acid (guest) and cyclodextrin coupled to hyaluronic acid. (host). The resulting hydrogel is thus physically linked only by reversible, non-covalent bonds.

Rodell et al., Advanced Functional Materials 25(4): 636-644 (2015) discloses a complicated procedure resulting in a guest-host complex between adamantane ester-coupled to hyaluronic acid (guest) and aminocyclodextrin amide-coupled to hyaluronic acid. (host), accompanied by thioether bonds between the hyaluronic acid molecules. The resulting hydrogel is thus physically linked by reversible, non-covalent bonds and cross-linked by thioether bonds.

Li et al., Scientific Reports 4: 4164 (2014) discloses a complicated procedure resulting in a guest-host complex between adamantane coupled to gold particles (guest) and cyclodextrin coupled to hyaluronic acid (host). The gold particles are thus physically linked to the hyaluronic acid only by reversible, non-covalent bonds

SUMMARY OF THE INVENTION

It is an object of the present invention to provide improved formulations for administration of pharmaceutical and/or cosmetic substances, and preferably for administration of retinoid substances or retinoic acid metabolism blocking agents (RAMBAs).

In particular, it is an object of the present invention to provide a stable cross-linked hyaluronic acid gel product having a significant amount of grafted cyclodextrins complexed with active drug substances, and preferably with retinoid or RAMBA substances.

It is also an object of the present invention to provide a process for preparing improved formulations for administration of pharmaceutical and/or cosmetic substances, and preferably for administration of retinoid or RAMBA substances.

It is an object of the present invention to provide an improved formulation with controlled release of pharmaceutical and/or cosmetic substances, and preferably for controlled release of retinoid or RAMBA substances.

It is also an object of the present invention to provide a simple and robust procedure for providing a system for controlled release of retinoid or RAMBA substances, in particular adapalene.

It is a further object of the present invention to provide a system for controlled release of retinoid or RAMBA substances, in particular adapalene, with a low degradation rate and long shelf-life.

In particular, it is an object of the present invention to a process for providing a stable cross-linked hyaluronic acid gel product having a significant amount of grafted cyclodextrins complexed with active drug substances, and preferably with retinoid or RAMBA substances.

For these and other objects that will be evident from this disclosure, the present invention provides according to a first aspect a hyaluronic acid product comprising a cross-linked hyaluronic acid and one or more cyclodextrin molecules, wherein the hyaluronic acid is cross-linked by ether bonds and wherein the one or more cyclodextrin molecules are grafted onto the cross-linked hyaluronic acid by amide bonds between an amino group of the aminocyclodextrin molecule(s) and a carboxyl group of the cross-linked hyaluronic acid; and further comprising a guest molecule capable of forming a guest-host complex with the aminocyclodextrin molecule acting as a host, wherein the guest molecule is a retinoid, such as adapalene or trifarotene, or a RAMBA, such as 4-(2-((5,5,8,8-tetramethyl-5,6,7,8-tetrahydronaphthalen-2-yl)sulfonyl)ethyl)benzoic acid. The guest molecule is preferably selected from the group consisting of adapalene, trifarotene and 4-(2-((5,5,8,8-tetramethyl-5,6,7,8-tetrahydronaphthalen-2-yl)sulfonyl)ethyl)benzoic acid.

It has surprisingly been realized that grafting of the cyclodextrin molecules onto the already cross-linked hyaluronic acid by amide bonds is associated with a low degree of depolymerization of the cross-linked hyaluronic acid. Without desiring to be bound by any specific mechanism, it is contemplated that the ether bonds contribute to stability of the already cross-linked hyaluronic acid: It is also considered that the ether bonds contribute to the stability of the product to degradation in an aqueous environment, providing a long shelf-life of an aqueous product.

It is advantageous to graft the cyclodextrin molecules on already cross-linked hyaluronic acid, which may already be prepared in a desirable form having defined physico-chemical properties. This allows for a significant modification of cross-linked HA with cyclodextrins with limited depolymerization of the cross-linked HA.

According to a preferred embodiment, the cross-linked hyaluronic acid product is in the form of gel particles having an average size in the range of 0.01-5 mm, preferably 0.1-0.8 mm.

According to one preferred embodiment, the hyaluronic acid chains are cross-linked to each other via a linking group which is derived from a bi- or polyfunctional cross-linking agent, such as a diglycidyl ether, e.g. 1,4-butanediol diglycidyl ether (BDDE).

According to a preferred embodiment, the cyclodextrin molecule contains a linking group having an amino group, and wherein the linking group of the cyclodextrin molecule forms said amide bond with a carboxyl group of the cross-linked hyaluronic acid. Certain linking groups contain a $C_{1-6}$ alkyl or $C_{1-6}$ alkyl linker.

According to another preferred embodiment, the cyclodextrin molecules are aminocyclodextrins, such as $\alpha$-, $\beta$- or $\gamma$-cyclodextrins, of which 2-aminocyclodextrin, 3-aminocyclodextrin and 6-aminocyclodextrin are preferred. As used herein, the term aminocyclodextrins refers to cyclodextrins having an amino group on the cyclodextrin backbone, i.e. without any linking group between the cyclodextrin backbone and the amine group. The resulting direct amide bond between hyaluronic acid and the cyclodextrin via its amino group is advantageous for achieving a slow release profile from the grafted cyclodextrin.

The aminocyclodextrin can also be functionalized with small alkyl ($C_{1-4}$) groups on hydroxyl positions. Aminocyclodextrin functionalized with methyl groups or hydroxypropyl groups are preferred.

The hyaluronic acid product is further comprising a guest molecule capable of forming a guest-host complex with the cyclodextrin molecule acting as a host. The guest molecule is a retinoid selected from the group consisting of adapalene and trifarotene, or a RAMBA selected from 4-(2-((5,5,8,8-tetramethyl-5,6,7,8-tetrahydronaphthalen-2-yl)sulfonyl)ethyl)benzoic acid.

A preferred retinoid according to the invention is adapalene.

Another preferred retinoid according to the invention is trifarotene.

A preferred RAMBA according to the invention is 4-(2-((5,5,8,8-tetramethyl-5,6,7,8-tetrahydronaphthalen-2-yl)sulfonyl)ethyl)benzoic acid.

According to a related aspect, the present invention provides a process of preparing a formulation of a guest molecule capable of forming a guest-host complex with a cyclodextrin host molecule, comprising the steps:

(a) providing (i) hyaluronic acid and (ii) one or more cyclodextrin host molecules capable of forming a guest-host complex with the guest molecule;
(b) cross-linking the hyaluronic acid by ether bonds using a bi- or polyfunctional cross-linking agent;
(c) grafting the one or more cyclodextrin host molecules onto the cross-linked hyaluronic acid by amide bonds; and
d) bringing a solution of the guest molecule into contact with the cyclodextrin host molecules grafted onto the cross-linked hyaluronic acid under conditions allowing for the formation of a guest-host complex between the cyclodextrin host molecules and the guest molecule, and optionally
e) recovering the guest-host complex bound to the cross-linked hyaluronic acid;
wherein the guest molecule is a retinoid selected from the group consisting of adapalene and trifarotene, or a RAMBA selected from 4-(2-((5,5,8,8-tetramethyl-5,6,7,8-tetrahydronaphthalen-2-yl)sulfonyl)ethyl)benzoic acid.

A preferred retinoid according to the invention is adapalene.

Another preferred retinoid according to the invention is trifarotene.

A preferred RAM BA according to the invention is 4-(2-((5,5,8,8-tetramethyl-5,6,7,8-tetrahydronaphthalen-2-yl)sulfonyl)ethyl)benzoic acid.

It has surprisingly been realized that grafting of the cyclodextrin molecules onto the already cross-linked hyaluronic acid by amide bonds is associated with a low degree of depolymerization of the cross-linked hyaluronic acid.

According to a preferred embodiment, the cyclodextrin molecule contains a linking group having an amino group, and wherein the linking group of the cyclodextrin molecule forms said amide bond with a carboxyl group of the cross-linked hyaluronic acid. Certain linking groups contain a $C_{1-6}$ alkyl or $C_{1-6}$ alkyl linker.

According to another preferred embodiment, the cyclodextrin molecules are aminocyclodextrins, such as .α-, β- or γ-cyclodextrins, of which 2-aminocyclodextrin, 3-aminocyclodextrin and 6-aminocyclodextrin are preferred. The resulting direct amide bond between hyaluronic acid and the cyclodextrin via its amino group is advantageous for achieving a slow release profile from the grafted cyclodextrin.

The aminocyclodextrin can also be functionalized with small alkyl ($C_{1-4}$) groups on hydroxyl positions. Aminocyclodextrin functionalized with methyl groups or hydroxypropyl groups are preferred.

In a preferred embodiment, the grafting of step (c) involves:
(i) activating the carboxyl groups on the cross-linked hyaluronic acid with a peptide coupling reagent to form an activated, cross-linked hyaluronic acid; and
(ii) coupling the linking group of the one or more cyclodextrin molecules to the carboxyl groups of the activated cross-linked hyaluronic acid by amide bonds.

In one preferred embodiment, the peptide coupling reagent is selected from the group consisting of triazine-based coupling reagents, carbodiimide coupling reagents, imidazolium-derived coupling reagents, Oxyma and COMU. The peptide coupling reagent is preferably a triazine-based coupling reagent, such as 2-chloro-4,6-disubstituted-1,3,5-triazines in the presence of a tertiary amine base or the corresponding quarternary ammonium salts thereof, such as 2-chloro-4,6-dimethoxy-1,3,5-triazin (CDMT) together with N-methylmorpholine (NMM), or 4-(4,6-dimethoxy-1,3,5-triazin-2-yl)-4-methylmorpholinium chloride (DMTMM), and preferably DMTMM.

Other aspects and preferred embodiments of the present invention will be evident from the following detailed disclosure of the invention and the appended claims.

DETAILED DESCRIPTION OF THE INVENTION

Figure 1:
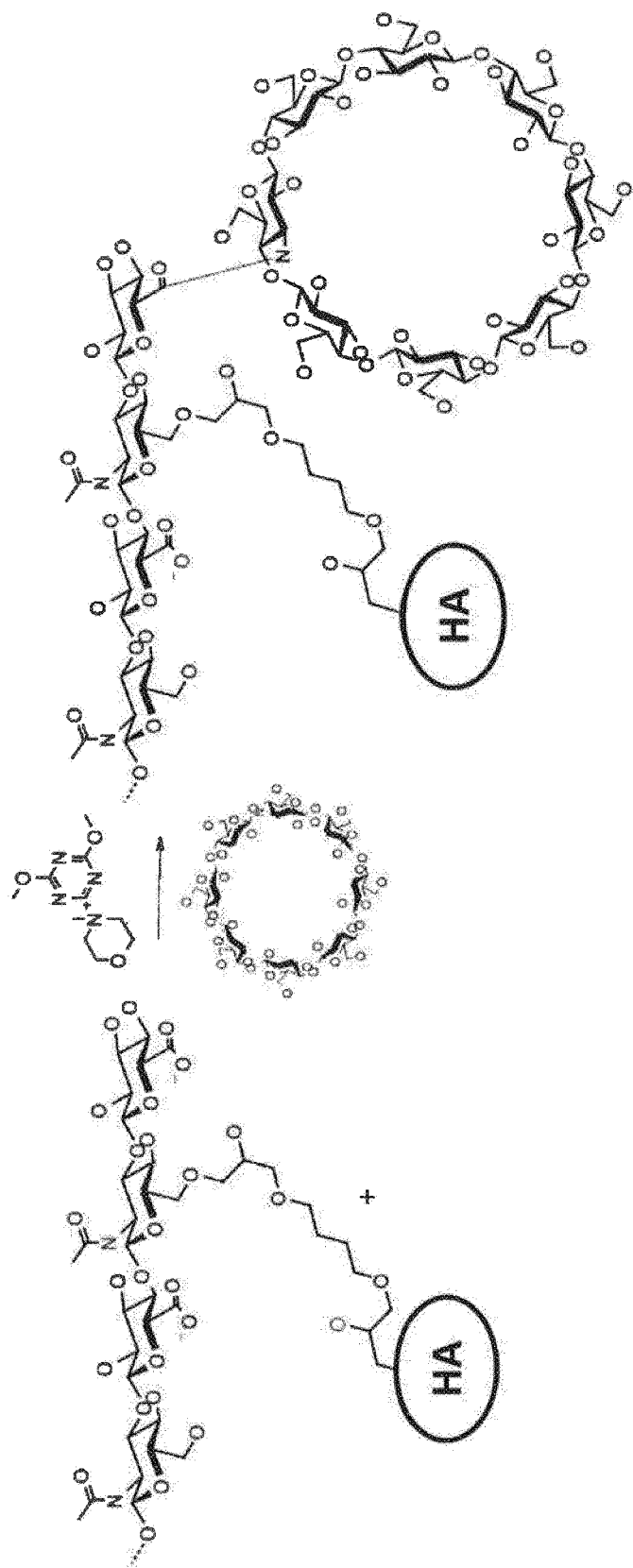
FIG. 1 shows grafting of amino-cyclodextrin to cross-linked HA using the peptide coupling reagent DMTMM.

The present invention generally provides cross-linked hyaluronic acid gel with cyclodextrin molecules grafted thereto; and further comprising a guest molecule capable of forming a guest-host complex with the aminocyclodextrin molecule acting as a host. The hyaluronic acid product is comprising a cross-linked hyaluronic acid and one or more cyclodextrin molecules, wherein the hyaluronic acid is cross-linked by ether bonds and wherein the one or more cyclodextrin molecules are grafted onto the cross-linked hyaluronic acid by amide bonds. This is achieved by a two-step process which is advantageous for avoiding massive depolymerization of the cross-linked hyaluronic acid. The guest molecule is a retinoid or a RAMBA.

Unless otherwise provided, the term "hyaluronic acid" encompasses all variants and combinations of variants of hyaluronic acid, hyaluronate or hyaluronan, of various chain lengths and charge states, as well as with various chemical modifications. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of CHO to —$CH_2OH$ or coupling with amines to form imines followed by reduction to secondary amines; sulphation; deamidation, optionally followed by deamination or amide formation with new acids; esterification; and deacetylation. Other examples of modifications are isourea, hydrazide, bromocyan, monoepoxide and monosulfone couplings.

For avoidance of doubt, the hyaluronic acid is not cross-linked to any further polymer, such as a polysaccharide or a glycosaminoglycan. Specifically, the hyaluronic acid is not cross-linked to dextran.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments, the concentration of the cross-linked hyaluronic acid is in the range of 1 to 100 mg/ml. In some embodiments the concentration of the cross-linked hyaluronic acid is in the range of 2 to 50 mg/ml. In specific embodiments the concentration of the cross-linked hyaluronic acid is in the range of 5 to 30 mg/ml or in the range of 10 to 30 mg/ml.

Cross-linked hyaluronic acid comprises cross-links between the hyaluronic acid chains, which creates a continuous network of hyaluronic acid molecules which is held together by the covalent cross-links, physical entangling of the hyaluronic acid chains and various interactions, such as electrostatic interactions, hydrogen bonding and van der Waals forces.

The cross-linked hyaluronic acid product is preferably biocompatible. This implies that no, or only very mild, immune response occurs in the treated individual. That is, no or only very mild undesirable local or systemic effects occur in the treated individual.

The cross-linked hyaluronic acid product according to the invention may be a gel, or a hydrogel. That is, it can be regarded as a water-insoluble, but substantially dilute cross-linked system of hyaluronic acid molecules when subjected to a liquid, typically an aqueous liquid.

The gel contains mostly liquid by weight and can e.g. contain 90-99.9% water, but it behaves like a solid due to a three-dimensional cross-linked hyaluronic acid network within the liquid. Due to its significant liquid content, the gel is structurally flexible and similar to natural tissue, which makes it very useful as a scaffold in tissue engineering and for tissue augmentation.

Cross-linking of the hyaluronic acid may be achieved by modification with a cross-linking agent. The hyaluronic acid concentration and the extent of cross-linking affects the mechanical properties, e.g. the elastic modulus G', and stability properties of the gel. Cross-linked hyaluronic acid gels are often characterized in terms of "degree of modification". The degree of modification of hyaluronic acid gels generally range between 0.1 and 15 mole %. The degree of modification (mole %) describes the amount of cross-linking agent(s) that is bound to HA, i.e. molar amount of bound cross-linking agent(s) relative to the total molar amount of repeating HA disaccharide units. The degree of modification reflects to what degree the HA has been chemically modified by the cross-linking agent. Reaction conditions for cross-linking and suitable analytical techniques for determining the degree of modification are all well known to the person skilled in the art, who easily can adjust these and other relevant factors and thereby provide suitable conditions to obtain a degree of modification in the range of 0.1-2% and verify the resulting product characteristics with respect to the degree of modification. A BDDE (1,4-butandiol diglycidylether) cross-linked hyaluronic acid gel may for example be prepared according to the method described in Examples 1 and 2 of published international patent application WO 9704012.

In a preferred embodiment, the cross-linked hyaluronic acid is present in the form of a gel cross-linked by a crosslinking agent, wherein the concentration of said hyaluronic acid is in the range of 10 to 30 mg/ml, and the degree of modification with said cross-linking agent is in the range of 0.1 to 2 mole %.

Hyaluronic acid gels may also comprise a portion of hyaluronic acid which is not cross-linked, i.e not bound to the three-dimensional crosslinked hyaluronic acid network. However, it is preferred that at least 50% by weight, preferably at least 60% by weight, more preferably at least 70% by weight, and most preferably at least 80% by weight, of the hyaluronic acid in a gel composition form part of the crosslinked hyaluronic acid network.

The hyaluronic acid product is present in the form of particles, strings, discs, etc. In a preferred embodiment, the cross-linked hyaluronic acid is in the form of gel particles. The gel particles preferably have an average size in the range of 0.01-5 mm, preferably 0.1-0.8 mm, such as 0.2-0.5 mm or 0.5-0.8 mm.

The hyaluronic acid product may be present in an aqueous solution, but it may also be present in dried or precipitated form, e.g. in ethanol. The hyaluronic acid product is preferably injectable.

The hyaluronic acid chains are cross-linked to each other via a linking group which is derived from a bi- or polyfunctional cross-linking agent. The bi- or polyfunctional cross-linking agent of the hyaluronic acid composition connects the hyaluronic acid chains to each other. The bi- or polyfunctional crosslinking agent further acts as a spacer between the hyaluronic acid chains.

The bi- or polyfunctional crosslinking agent comprises two or more functional groups capable of reacting with functional groups of the hyaluronic acid, resulting in the formation of covalent bonds. The bi- or polyfunctional crosslinking agent may for example selected from the group consisting of divinyl sulfone, multiepoxides and diepoxides.

A preferred type of bi- or polyfunctional cross-linking agent is a bis- or polyepoxide, such as a diglycidyl ether. According to an embodiment, the bi- or polyfunctional crosslinking agent comprises two or more glycidyl ether functional groups. The glycidyl ether functional groups react with primary hydroxyl groups of the hyaluronic acid, resulting in the formation of ether bonds under neutral or basic conditions. It follows that when a diglycidyl ether cross-linking agent reacts with the primary hydroxyl groups of hyaluronan, two ether bonds are formed with an intermediate spacer remaining from the cross-linking agent.

Preferred bi- or polyfunctional cross-linking agent for cross-linking the hyaluronic acid chains include 1,4-butanediol diglycidyl ether (BDDE), 1,2-bis(2,3-epoxypropoxy) ethylene (EGDGE) and ethylene glycol diglycidyl ether (EGDE), 1,2-ethanediol diglycidyl ether (EDDE) and diepoxyoctane. A particularly preferred bi- or polyfunctional cross-linking agent is BDDE.

A critical feature of the present invention is that the cyclodextrin molecules are grafted onto the cross-linked hyaluronic acid by amide bonds. Thus, the present invention allows for a mild coupling reaction producing an amide bond between the cyclodextrin and cross-linked hyaluronic acid with defined physico-chemical properties, e.g. in particle form. The resulting cross-linked hyaluronic acid product has useful stability properties and is thus suitable for slow-release applications. Another advantage of the present invention is that the grafting of cyclodextrin molecules via an amide bond to ether cross-linked hyaluronic acid allows for a significant modification of the cross-linked hyaluronic acid with cyclodextrins without inducing massive depolymerization thereof. It is preferred that the cyclodextrin molecules and the disaccharides of the cross-linked hyaluronic acid have a molar ratio of 0.1-50%, preferably 1-30%, such as 1-20%. It is also preferred that the cyclodextrin molecules and the disaccharides of the cross-linked hyaluronic acid have a molar ratio of more than 2%, such as more than 5%.

The cyclodextrin molecules are used as carriers (hosts) for a pharmaceutical agent (guest). When a pharmaceutical agent (the guest) is contained, fully or partially, within the interior of the cyclodextrin (the host), this is referred to as an inclusion complex or guest/host complex. The cyclodextrin may then release the pharmaceutical agent under specific conditions, e.g. due to change in pH leading to the cleavage of hydrogen or ionic bonds between the host and the guest molecules.

The cyclodextrin molecules are attached to the hyaluronic acid in order to reduce migration of the cyclodextrin (or guest/host complex) from the site of administration, e.g. injection. In this way, the site of release of the pharmaceutical agent from the cyclodextrin can be controlled.

Also, in order to increase temporal control of the release of the pharmaceutical agent, it has been found that the influence of cleavage of the bonds between the cyclodextrin (or guest/host complex) and the hyaluronic acid should be minimized. In other words, it is desired that the release of the pharmaceutical agent is, as far as possible dependent on the physical release from the cyclodextrin rather than on chemical degradation.

In the disclosed hyaluronic acid products, the cyclodextrin molecules are attached to the hyaluronic acid by amide bonds. The use of amide bonds in the cyclodextrin-hyaluronic acid linkage (graft) has been found to be advantageous compared to e.g. ester bonds, since the amide bond is more stable to degradation in vivo. The use of a less stable bond between the hyaluronic acid and cyclodextrin molecules could lead to premature loss of cyclodextrin (or guest/host complex) from the site of injection.

The cyclodextrin of the hyaluronic acid product may in practice be any cyclodextrin capable of acting as the host molecule in a guest/host complex together with a pharmaceutical agent. Cyclodextrins may generally be constituted by 5-32 glucopyranoside units. However, cyclodextrins constituted by 6-8 glucopyranoside units are generally preferred for the formation of guest/host complexes with pharmaceutical agents. Cyclodextrins constituted by 6, 7 and 8 glucopyranoside units are often referred to as α-, β- and γ-cyclodextrins respectively. According to an embodiment, the cyclodextrin molecules are constituted by 6 glucopyranoside units (α-cyclodextrin). According to an embodiment, the cyclodextrin molecules are constituted by 7 glucopyranoside units (β-cyclodextrin). According to an embodiment, the cyclodextrin molecules are constituted by 8 glucopyranoside units (γ-cyclodextrin).

Cyclodextrins are often chemically modified in order to improve their solubility in water and/or to optimize their performance in a specific application. The term cyclodextrin, α-cyclodextrin, β-cyclodextrin and γ-cyclodextrin, as used herein is also intended to encompass the functionally equivalent variants or derivatives thereof. Examples of such chemically modified cyclodextrins include, but are not limited to, hydroxypropyl and methyl cyclodextrins.

Examples of modified α-cyclodextrins for use with the hyaluronic acid composition include, but are not limited to, hydroxypropyl-α-cyclodextrin.

Examples of modified β-cyclodextrins for use with the hyaluronic acid composition include, but are not limited to, hydroxypropyl-β-cyclodextrin; 2,6-di-O-methyl-β-cyclodextrin; 6-O-maltosyl-β-cyclodextrin; 2-hydroxypropyl-β-cyclodextrin; methyl-β-cyclodextrin; sulfobutyl-β-cyclodextrin; monochlorotriazinyl-β-cyclodextrin; heptakis (2-w-amino-O-oligo (ethylene oxide)-6-hexylthio)-β-cyclodextrin; ethylenediamino or diethylenetriamino bridged bis(β cyclodextrin)s; randomly methylated β-cyclodextrin; sulfobutyl ether-β-cyclodextrin; and monochlorotriazinyl-β-cyclodextrin.

Examples of modified γ-cyclodextrins for use with the hyaluronic acid composition include, but are not limited to, γ-cyclodextrin C6, and 2,3-di-O-hexanoyl-γcyclodextrin.

According to the invention, it is preferred that the cyclodextrin molecule contains a linking group having an amino group. The linking group is covalently attached to the cyclodextrin backbone and may include a spacer molecule, such as $C_{1-6}$ alkyl or $C_{1-4}$ alkyl. The linking group of the cyclodextrin molecule forms an amide bond with a carboxyl group of the cross-linked hyaluronic acid.

In a preferred embodiment, the cyclodextrin molecule is an aminocyclodextrin molecule, i.e. having an amino group on the cyclodextrin backbone, and the amino group of the aminocyclodextrin molecule forms the amide bond with a carboxyl group of the cross-linked hyaluronic acid. As used herein, the term aminocyclodextrins refers to cyclodextrins having an amino group on the cyclodextrin backbone, i.e. without any linking group between the cyclodextrin backbone and the amine group. Thereby, a direct amide bond is achieved between the cyclodextrin and the ether cross-linked HA. The resulting direct amide bond between hyaluronic acid and the cyclodextrin via its amino group is advantageous for achieving a slow release profile from the grafted cyclodextrin.

A preferred group of cyclodextrin molecules are aminocyclodextrin molecules constituted by 6-8 glucopyranoside units, such as 6 glucopyranoside units (α-cyclodextrin), 7 glucopyranoside units (β-cyclodextrin) or 8 glucopyranoside units (γ-cyclodextrin). It is then furthermore preferred that the cyclodextrin molecule is selected from the group consisting of 2-aminocyclodextrin, 3-aminocyclodextrin and 6-aminocyclodextrin, preferably from the group consisting of 3-aminocyclodextrin and 6-aminocyclodextrin.

The aminocyclodextrin can also be functionalized with small alkyl ($C_{1-4}$) groups on hydroxyl positions. Aminocyclodextrin functionalized with methyl groups or hydroxypropyl groups are preferred.

The hyaluronic acid product disclosed is used for the transport or administration and slow or controlled release of various pharmaceutical or cosmetic substances.

The hyaluronic acid product comprises a guest molecule capable of forming a guest-host complex with the cyclodextrin molecule acting as a host. For avoidance of doubt, the guest molecule is a small drug molecule which is not covalently linked to any other molecule or polymer.

The guest molecule is preferably a retinoid selected from the group consisting of adapalene and trifarotene, or a RAMBA selected from 4-(2-((5,5,8,8-tetramethyl-5,6,7,8-tetrahydronaphthalen-2-yl)sulfonyl)ethyl)benzoic acid.

A particularly preferred retinoid guest molecule is adapalene, CAS Registry Number: 106685-40-9. Adapalene is 6-[3-(1-adamantyl)-4-methoxy-phenyl] naphthalene-2-carboxylic acid (I):

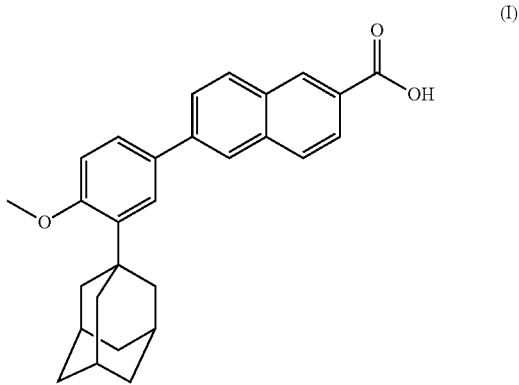 [SMILES: COc1ccc(-c2ccc3cc(C(=O)O)ccc3c2)cc1C12CC3CC(CC(C3)C1)C2]

Adapalene inhibits keratinocyte differentiation and proliferation. This inhibition of keratinocyte differentiation and proliferation is responsible for adapalene's comedolytic effect. It has both exfoliating and anti-inflammatory effects.

Another particularly preferred retinoid guest molecule is trifarotene. Trifarotene is 3"-(tert-butyl)-4'-(2-hydroxyethoxy)-4"-(pyrrolidin-1-yl)-[1,1':3',1"-terphenyl]-4-carboxylic acid (II):

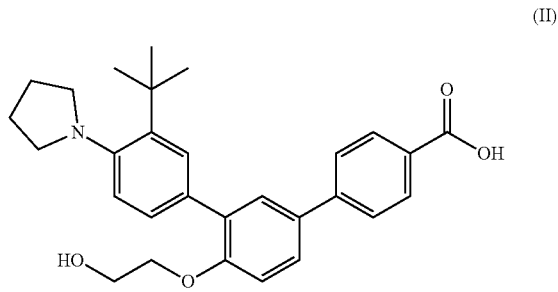 [SMILES: CC(C)(C)c1cc(-c2cc(-c3ccc(C(=O)O)cc3)ccc2OCCO)ccc1N1CCCC1]

A preferred RAMBA guest molecule is 4-(2-((5,5,8,8-tetramethyl-5,6,7,8-tetrahydronaphthalen-2-yl)sulfonyl) ethyl)benzoic acid (III):

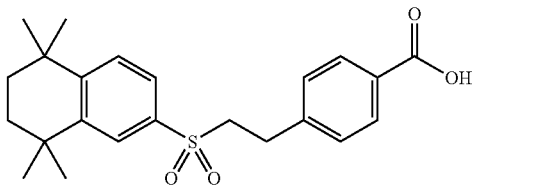

(III)

The hyaluronic acid product according to the invention is thus useful as a medicament, e.g. in the treatment of a condition susceptible to treatment by said guest molecule.

The hyaluronic acid product is also useful for the manufacture of a medicament for treatment of a condition susceptible to treatment by said guest molecule.

According to one aspect, the hyaluronic acid product is useful in a method of treating a patient suffering from a condition susceptible to treatment by a guest molecule, by administering to the patient a therapeutically effective amount of a hyaluronic acid product according to the invention comprising said guest molecule.

According to another aspect, the hyaluronic acid product is useful in a method of cosmetically treating skin, which comprises administering to the skin a hyaluronic acid product according to the invention.

Since the nature of the product obtainable or obtained by the processes according to the invention is complex, the product may also be defined as being the result of these processes.

The insights presented herein are also useful in a process of preparing a formulation of a guest molecule capable of forming a guest-host complex with a cyclodextrin host molecule, comprising the steps:
(a) providing (i) hyaluronic acid and (ii) one or more cyclodextrin host molecules capable of forming a guest-host complex with the guest molecule;
(b) cross-linking the hyaluronic acid by ether bonds using a bi- or polyfunctional cross-linking agent;
(c) grafting the one or more cyclodextrin host molecules onto the cross-linked hyaluronic acid by amide bonds; and
d) bringing a solution of the guest molecule into contact with the cyclodextrin host molecules grafted onto the cross-linked hyaluronic acid under conditions allowing for the formation of a guest-host complex between the cyclodextrin host molecules and the guest molecule, and optionally
e) recovering the guest-host complex bound to the cross-linked hyaluronic acid.

Preferred embodiments of steps (a) and (b) are evident from the description above relating to the resulting product. In particular, step (b) may further comprise size reduction of the cross-linked hyaluronic acid into particles, strings, discs, etc. In a preferred embodiment, the cross-linked hyaluronic acid is brought into the form of gel particles. The hyaluronic acid gel particles are obtained by reaction of hyaluronic acid and a cross-linking reagent, e.g. BDDE under standard conditions. Particle size reduction of the resulting hydrogel followed by precipitation in ethanol induce the formation of such particles. The gel particles preferably have an average swelled size in the range of 0.01-5 mm, preferably 0.1-0.8 mm, such as 0.2-0.5 mm or 0.5-0.8 mm.

It is preferred that the one or more cyclodextrin molecules of step (a) contain a linking group having an amino group, and wherein the linking group of the cyclodextrin molecule forms said amide bond with a carboxyl group of the cross-linked hyaluronic acid. The linking group may contain a spacer, such as $C_{1-6}$ alkyl or $C_{1-4}$ alkyl.

It is also preferred that the one or more cyclodextrin molecules are aminocyclodextrin molecules as disclosed hereinabove, i.e. having an amino group on the cyclodextrin backbone. As used herein, the term aminocyclodextrins refers to cyclodextrins having an amino group on the cyclodextrin backbone, i.e. without any linking group between the cyclodextrin backbone and the amine group. In a preferred process, the cyclodextrin molecule is an aminocyclodextrin molecule, and an amino group of the aminocyclodextrin molecule forms said amide bond with a carboxyl group of the cross-linked hyaluronic acid. The resulting direct amide bond between hyaluronic acid and the cyclodextrin via its amino group is advantageous for achieving a slow release profile from the grafted cyclodextrin.

In a preferred process, the grafting of step (c) involves:
(i) activating the carboxyl groups on the cross-linked hyaluronic acid with a peptide coupling reagent to form an activated, cross-linked hyaluronic acid; and
(ii) coupling the linking group of the one or more cyclodextrin molecules to the carboxyl groups of the activated cross-linked hyaluronic acid by amide bonds.

It has inventively been realized that the use of triazine-based coupling reagents on cross-linked hyaluronic acid, such as preformed HA particles, with defined physicochemical properties allow for a significant modification (grafting) of cross-linked HA with cyclodextrins via amide bonds without inducing massive depolymerization of the cross-linked hyaluronic acid. This is verified in Example 12, wherein the swelling capacity, i.e. total liquid uptake per gram HA, was observed to decrease linearly with increasing $MOD_{CDx/HADi}$. This linear behaviour demonstrates that grafting cyclodextrins on an ether cross-linked HA gel using a triazine-coupling reagent does not induce any pronounced degradation of the HA gel. This is in contrast to the situation when the cross-linking is performed on cyclodextrin-grafted hyaluronic acid chains, which may induce a massive depolymerization of the polysaccharide.

The one or more cyclodextrin molecules, such as aminocyclodextrin molecules, and the disaccharides of the cross-linked hyaluronic acid of the resulting hyaluronic acid product may have a molar ratio of 0.1-50%, preferably 1-30% or 1-20%. It is also preferred that the cyclodextrin molecules and the disaccharides of the cross-linked hyaluronic acid have a molar ratio of more than 2%, such as more than 5%.

The process typically results in a low degree of depolymerization of the cross-linked hyaluronic acid.

In the process, the activation of the cross-linked hyaluronic acid and the coupling of the cyclodextrin molecule to the activated cross-linked hyaluronic acid may occur simultaneously in step (c). Alternatively, the activation of the cross-linked hyaluronic acid occurs prior to and separately from the coupling of the cyclodextrin molecule to the activated cross-linked hyaluronic acid in step (c).

Preferred peptide coupling reagents are selected from the group consisting of triazine-based coupling reagents, carbodiimide coupling reagents, imidazolium-derived coupling reagents, Oxyma and COMU. Various other useful peptide coupling reagents are well known to the skilled person.

A particularly preferred group of peptide coupling reagent are triazine-based coupling reagents, such as 2-chloro-4,6-disubstituted-1,3,5-triazines in the presence of a tertiary amine base or the corresponding quarternary ammonium salts thereof, such as 2-chloro-4,6-dimethoxy-1,3,5-triazine (CDMT) together with N-methylmorpholine (NMM), or 4-(4,6-dimethoxy-1,3,5-triazin-2-yl)-4-methylmorpholinium chloride (DMTMM). A particularly preferred triazine-based coupling reagent is DMTMM.

In a preferred embodiment, the amide bonds are formed between the amino group of amino-cyclodextrins having 6-8 glucopyranoside units and the carboxylic acid group of ether cross-linked hyaluronic acid gel particles. This amide bond between the two components is realized by a peptide coupling agent, such as DMTMM.

The guest molecule is preferably a retinoid selected from the group consisting of adapalene and trifarotene, or a RAMBA selected from 4-(2-((5,5,8,8-tetramethyl-5,6,7,8-tetrahydronaphthalen-2-yl)sulfonyl)ethyl)benzoic acid.

A particularly preferred retinoid guest molecule is adapalene, CAS Registry Number: 106685-40-9. Adapalene is 6-[3-(1-adamantyl)-4-methoxy-phenyl] naphthalene-2-carboxylic acid (I):

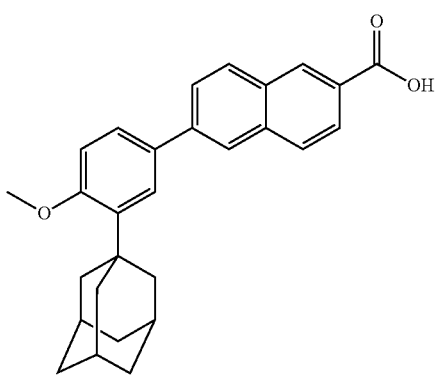

Adapalene inhibits keratinocyte differentiation and proliferation. This inhibition of keratinocyte differentiation and proliferation is responsible for adapalene's comedolytic effect. It has both exfoliating and anti-inflammatory effects.

Another particularly preferred retinoid guest molecule is trifarotene. Trifarotene is 3"-(tert-butyl)-4'-(2-hydroxyethoxy)-4"-(pyrrolidin-1-yl)-[1,1':3',1"-terphenyl]-4-carboxylic acid (II):

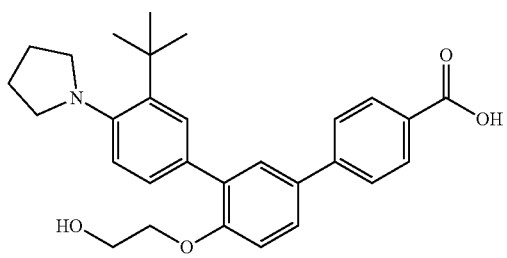

A preferred RAMBA guest molecule is 4-(2-((5,5,8,8-tetramethyl-5,6,7,8-tetrahydronaphthalen-2-yl)sulfonyl)ethyl)benzoic acid (III):

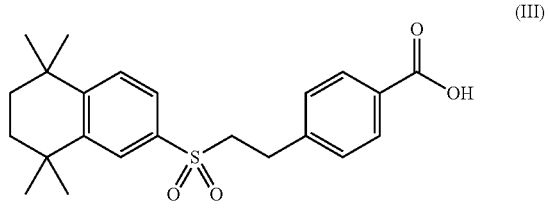 [SMILES: CC1(C)CCC(C)(C)c2cc(S(=O)(=O)CCc3ccc(C(=O)O)cc3)ccc21]

Without desiring to be limited thereto, the present invention will in the following be illustrated by way of examples.

EXAMPLES

Example 1—Grafting of 3-Amino-Gamma-CD to Dry Cross-Linked HA Powder

DMTMM (0.3 g) and 3-amino-gamma-CD (0.8 g) are dissolved in phosphate-buffered saline (PBS) (25 mL), and the pH of the solution is adjusted to approx. 6.5 (1.2 M HCl). This solution is added to dry cross-linked HA powder (0.5 g) and then stirred gently. The reaction is heated to 45° C. for 24 h and then allowed to cool down to room temperature. The gel is washed twice with PBS (15 mL/g gel) and filtrated. The gel is then washed three times with ethanol 70% (15 mL/g gel) and the solution is discarded. Finally, pure ethanol is added to the gel and filtrated and dried under vacuum to yield the final material.

Example 2—Grafting of 3-Amino-Beta-CD to Dry Cross-Linked HA Powder

DMTMM (0.2 g) and 3-amino-beta-CD (0.35 g) were dissolved in PBS (12.5 mL), and the pH of the solution was adjusted to approx. 6.5 (1.2 M HCl). This solution was added to dry ether cross-linked HA powder (0.3 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides to enable quantitative NMR analysis. 40-60 µL of a solution with Chondroitinase ABC from *Proteus vulgaris* was added to the gel sample which was further mixed and put on 37° C. incubation with gentle shaking for 24 h. After the incubation the degraded gel sample was lyophilized and re dissolved in 600 µL D$_2$O.

A 1D $^1$H quantitative NMR experiment was performed and the resulting spectrum was analyzed for determination of modification, measured as cyclodextrin over disaccharide, $MOD_{CDx/HAdi}$. Determination of $MoD_{CDx/HAdi}$ was done by comparison of the integrals from the signals of the anomeric protons from the cyclodextrin (CDx) to the N-acetyl protons from the GlcNAc of HA. The modification (cyclodextrin over disaccharide; $MOD_{CDx/HAdi}$) was 11% determined by $^1$H-NMR of enzymatically degraded gel.

Example 3—Grafting of 6-Amino-Beta-CD to Dry Ether Cross-Linked HA Powder

DMTMM (0.24 g) and 6-amino-beta-CD (0.3 g) were dissolved in PBS (15 mL), and the pH of the solution was adjusted to approx. 6.5 (1.2 M HCl). This solution was added to dry ether cross-linked HA powder (0.3 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. The modification (cyclodextrin over disaccharide; $MOD_{CDx/HAdi}$) was 22% determined by $^1$H-NMR of enzymatically degraded gel.

Example 4—Grafting of 6-Amino-Gamma-CD to Cross-Linked HA Gel

Dry HA powder (0.5 g) is dissolved in PBS (25 ml), and the pH of the solution is adjusted to approx. 9.0 using NaOH. Cross-linking reagent BDDE is added and allowed to react with the HA in solution, forming a gel. The gel is washed twice with PBS (15 mL/g gel) and filtrated. The gel is then washed three times with ethanol 70% (15 mL/g gel) and the solution is discarded.

DMTMM (0.3 g) and 3-amino-gamma-CD (0.8 g) are dissolved in phosphate-buffered saline (PBS) (25 mL), and the pH of the solution is adjusted to approx. 6.5 (1.2 M HCl). This solution is added to the cross-linked HA gel and then stirred gently. The reaction is heated to 45° C. for 24 h and then allowed to cool down to room temperature. The gel is washed twice with PBS (15 mL/g gel) and filtrated. The gel is then washed three times with ethanol 70% (15 mL/g gel) and the solution is discarded. Finally, pure ethanol is added to the gel and filtrated and dried under vacuum to yield the final material.

Example 5 (Comparative)—Formation of a Hydrogel by Simultaneous Cross-Linking of Hyaluronan and Grafting of Gamma-Cyclodextrin HA (1.1 MDa) powder (0.25 g) and gamma cyclodextrin (0.25 g) were placed in a beaker. BDDE (0.024 g) was added to 3 g NaOH 1% (w/w). The BDDE/NaOH was added to the beaker. The molar ratio HADi:BDDE:CDx was 1:0.2:0.3. The components were mixed vigorously during 3.5 min. The reaction was allowed to proceed, and the paste was neutralized and swelled in phosphate buffer pH 7.4 for 24 h in 70° C. Particle size reduction was performed through a 315 urn screen. The gel was filled in syringes and sterilized.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 0.5% determined by $^1$H-NMR of enzymatically degraded gel.

Example 6 (Comparative)—Formation of a Hydrogel by Simultaneous Cross-Linking of Hyaluronan and Grafting of Gamma-Cyclodextrin HA (0.17 MDa) powder (0.4 g) and gamma-cyclodextrin (0.8 g) were dissolved in 1.8 g NaOH 1% (w/w) during 30 min in a syringe. In another syringe BDDE (0.12 g) was mixed with 0.6 g NaOH 1% (w/w). The molar ratio HADi:BDDE:CDx was 1:0.6:0.6. The two syringes were connected and the components were mixed by passing the connector 20 times. The formed paste was transferred to a vial temperated at 50° C. The reaction was allowed to proceed for 2.5 h at 50° C. 9 g PBS buffer containing HCl was added to neutralize and swell the gel before particle size reduction was done through a 60 urn screen between two syringes. The gel was precipitated and washed using ethanol.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 1.3% determined by $^1$H-NMR of enzymatically degraded gel.

Example 7—Grafting of 3-Monoamino-3-Monodeoxy-Gamma-Cyclodextrin to Dry Cross-Linked HA-Gel Powder DMTMM (0.17 g) and 3-monoamino-3-monodeoxy-gamma-cyclodextrin (0.61 g) were dissolved in PBS (12.5 mL), and the pH of the solution was adjusted to 6.5±2.5 (1.2 M HCl). The molar ratio HADi:DMTMM:CDx was 1:1:0.75. This solution was added to dry ether cross-linked HA powder (0.26 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 9% determined by $^1$H-NMR of enzymatically degraded gel.

Example 8—Grafting of 3-Monoamino-3-Monodeoxy-Beta-Cyclodextrin to Dry Cross-Linked HA-Gel Powder DMTMM (0.17 g) and 3-monoamino-3-monodeoxy-beta-cyclodextrin (0.35 g) were dissolved in PBS (12.5 mL), and the pH of the solution was adjusted to 6.5±2.5 (1.2 M HCl). The molar ratio HADi:DMTMM:CDx was 1:1:0.5. This solution was added to dry ether cross-linked HA powder (0.28 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 10% determined by $^1$H-NMR of enzymatically degraded gel.

Example 9—Grafting of 6-Monoamino-6-Monodeoxy-Beta-Cyclodextrin to Dry Cross-Linked HA-Gel Powder DMTMM (0.24 g) and 6-monoamino-6-monodeoxy-beta-cyclodextrin (0.31 g) were dissolved in PBS (15 mL), and the pH of the solution was adjusted to 6.5±2.5 (1.2 M HCl). The molar ratio HADi:DMTMM:CDx was 1:1.2:0.35. This solution was added to dry ether cross-linked HA powder (0.34 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 22% determined by $^1$H-NMR of enzymatically degraded gel.

Example 10—Grafting of 6-monoamino-6-monodeoxy-2-O-methyl-hexakis-(2,6-di-O-methyl)-beta-cyclodextrin to Dry Cross-Linked HA-Gel Powder DMTMM (0.24 g) 6-monoamino-6-monodeoxy-2-O-methyl-hexakis-(2,6-di-O-methyl)-beta-cyclodextrin (0.35 g) were dissolved in PBS (15 mL), and the pH of the solution was adjusted to 6.5±2.5 (1.2 M HCl) The molar ratio HADi:DMTMM:CDx was 1:1.2:0.35. This solution was added to dry ether cross-linked HA powder (0.34 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 23% determined by $^1$H-NMR of enzymatically degraded gel.

Example 11—Grafting of 6-Monohexamethylenediamino-6-Monodeoxy-Beta-Cyclodextrin to Dry Cross-Linked HA-Gel Powder DMTMM (0.24 g) 6-monohexamethylenediamino-6-monodeoxy-beta-cyclodextrin (0.65 g) were dissolved in PBS (15 mL), and the pH of the solution was adjusted to 6.5±2.5 (1.2 M HCl). The molar ratio HADi:DMTMM:CDx was 1:1.2:0.7. This solution was added to dry ether cross-linked HA powder (0.30 g) and was stirred gently. The reaction was heated to 45° C. for 24 h and then allowed to cool down to room temperature. The gel was washed twice with PBS (15 mL/g gel) and filtrated. The gel was washed three times with ethanol 70% (15 mL/g gel) and the solution was discarded. Finally, pure ethanol was added to the gel and filtrated and dried under vacuum to yield the final material.

The HA polymer was degraded into oligosaccharides, and a 1D $^1$H quantitative NMR experiment was performed as set out in Example 2. The resulting spectrum was analyzed for determination of $MoD_{CDx/HAdi}$. $MOD_{CDx/HADi}$ was 18% determined by $^1$H-NMR of enzymatically degraded gel.

Example 12—Grafting of 6-Monoamino-6-Monodeoxy-Beta-Cyclodextrin to Dry Cross-Linked HA-Gel Powder DMTMM and 6-monoamino-6-monodeoxy-beta-cyclodextrin (CDx) were varied for each experiment according to Table 4. The reagents were dissolved in phosphate buffer saline (PBS) (15 mL), and the pH of the solution was adjusted to 6.5±2.5 (1.2 M HCl). This solution was added to dry ether cross-linked HA powder and was stirred gently.

The reactions were heated to 45° C. for 24 h and then allowed to cool down to room temperature. The gels were washed twice with PBS (15 mL/g gel) and filtrated. The gels were washed three times with ethanol 70% (15 mL/g gel) and the solutions were discarded. Finally, pure ethanol was added to the gels and they were filtrated and dried under vacuum to yield the final materials.

The HA polymer was degraded into oligosaccharides, and a 1D $^1$H quantitative NMR experiment was performed as set out in Example 2. The resulting spectrum was analyzed for determination of $MoD_{CDx/HAdi}$. The resulting $MoD_{CDx/HADi}$ values are presented in Table 1.

TABLE 1

Impact of molar ratio DMTMM and CDx on $MoD_{CDx/HADi}$ values

| | g | | | mol equiv. | | | $MoD_{CDx/HADi}$ |
|---|---|---|---|---|---|---|---|
| Sample | HA | DMTMM | CDx | HA | DMTMM | CDx | (%) |
| A | 0.3 | 0.08 | 0.09 | 1 | 0.4 | 0.1 | 6 |
| B | 0.3 | 0.4 | 0.09 | 1 | 2 | 0.1 | 8 |
| C | 0.3 | 0.08 | 0.5 | 1 | 0.4 | 0.6 | 15 |
| D | 0.3 | 0.4 | 0.5 | 1 | 2 | 0.6 | 44 |
| E | 0.3 | 0.24 | 0.3 | 1 | 1.2 | 0.35 | 24 |
| F | 0.3 | 0.24 | 0.3 | 1 | 1.2 | 0.35 | 26 |

The swelling capacity, i.e. total liquid uptake per gram HA, was observed not to increase with increasing $MOD_{CDx/HADi}$. This behaviour demonstrates that grafting cyclodextrins on an ether cross-linked HA gel using a triazine-coupling reagent does not induce any pronounced degradation of the HA gel.

Example 13—Loading of Adapalene in HA-Gel Grafted with 2,6-Di-O-Methyl Beta Cyclodextrin A saturated gel slurry was made from precipitated HA-gel grafted with 2,6-di-O-methyl beta cyclodextrin (Example 10) and phosphate buffer. A stock solution of Adapalene in EtOH was added to the saturated gel. The amount EtOH in the composition was <40% (w/w) in order to avoid precipitation of gel particles. The gel with Adapalene was mixed end-over-end at 23° C. during 12 h (complexation time). After complexation the $EtOH/H_2O$ was removed by vacuum concentration (ScanVac, 30° C., 2000 rpm, 12 h) to yield a dry powder. The dry gel powder containing Adapalene was reconstituted in $H_2O$ to yield the final composition of HA (35 mg/mL) and Adapalene (0.02-0.10 mM). The gel powder with Adapalene was allowed to rest at different temperature and times prior to analysis (resting time).

TABLE 2

Complexation parameters

| Sample | Adapalene [mM] | Complexation time [time and temp] | Resting time [time and temp] |
|---|---|---|---|
| 13A | 0.02 | 12 h, 23° C. | 5 days, 23° C. |
| 13B | 0.02 | 12 h, 23° C. | 24 h, 70° C., then 4 days, 23° C. |
| 13C | 0.1 | 12 h, 23° C. | 6 days, 23° C. |

Figure 2:
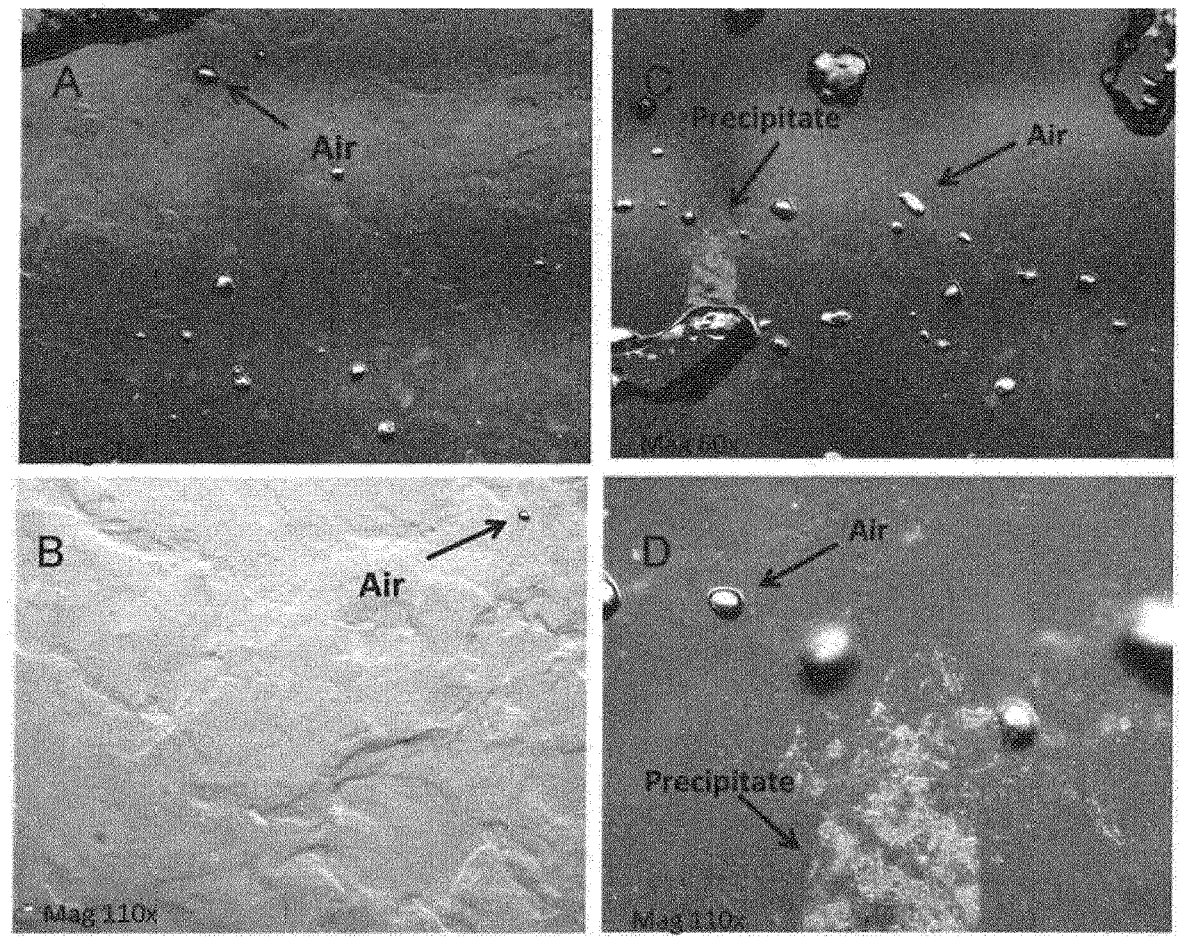
FIG. 2 shows micrographs of HA gels containing adapalene.

The gels were applied on a petri dish and a cover slip was applied. Pictures were acquired on a NIKON SMZ25 stereomicroscope. The obtained gels were transparent which indicates that Adapalene was dissolved in the composition. See FIG. 2A-B for illustrative micrographs of sample gel 13C.

Example 14—Loading of Adapalene in HA-Gel (Comparative)

A saturated gel slurry was made from precipitated HA gel without grafted cyclodextrin and phosphate buffer. A stock solution of Adapalene in EtOH was added to the saturated gel. The amount EtOH in the composition was <40% (w/w) in order to avoid precipitation of gel particles. The gel with Adapalene was mixed end-over-end at 23° C. during 12 h (complexation time). After complexation the EtOH/$H_2O$ was removed by vacuum concentration (ScanVac, 30° C., 2000 rpm, 12 h) to yield a dry powder. The dry gel powder containing Adapalene was reconstituted in $H_2O$ to yield the final composition of HA (35 mg/mL) and Adapalene 0.10 mM.

TABLE 3

Complexation parameters (comparative).

| Sample | Adapalene [mM] | Complexation time [time and temp] | Resting time [time and temp] |
|---|---|---|---|
| 14 | 0.1 | 12 h, 23° C. | 6 days, 23° C. |

The gel was applied on a petri dish and a cover slip was applied. Pictures were acquired on a NIKON SMZ25 stereomicroscope. The obtained gel was opaque which indicates that Adapalene precipitated in the composition. See FIG. 2C-D for illustrative micrographs of comparative sample gel 14.

Example 15—Release of Adapalene

Determination of Adapalene in Gel:

The adapalene content in the samples from Example 13 was determined using HPLC after extracting the adapalene from the gels. The gels were extracted by mixing 0.2 g or 0.7 g gel with 40 ml 40% ethanol. The extraction was made over night while stirring end over end. The adapalene content in the extract was determined using a HPLC method with fluorescence detection ($\lambda_{ex}$ 320 nm, $\lambda_{em}$ 425 nm). The compound was eluted using a C18 column and a gradient ranging from 30% to 90% of organic phase in aqueous trifluoroacetic acid.

Release Study:

The release of adapalene from gels A and B from example 13 were measured in duplicates. 1 ml gel was loaded into gel-containers in a 3 mm thick layer with a surface area of 3.2 cm². The surface was covered with a plastic net with a mesh size of 60 μm. The gel containers were placed in 1000 ml release media (0.9% NaCl with 10 mM phosphate buffer) in a USP paddle bath. The amount of adapalene in the gels was determined before the release experiment started (an average from duplicate measurements) and in the gels after 9 days of release. The results are given in Table 4. After 9 days of release into a saline solution only about 35% of the Adapalene has been released. For comparison: A small drug dissolved in a gel without cyclodextrin is completely released after 6 hours in this experimental set up.

TABLE 4

Adapalene release

| Sample | Adapalene in gel | Adapalene in gel after 9 days | Decrease (%) |
|---|---|---|---|
| A-1 | 22.4 | 14.5 | 35 |
| A-2 |  | 14.1 | 37 |
| B-1 | 20.8 | 13.6 | 35 |
| B-2 |  | 13.7 | 34 |

Conclusion: The gel containing bound cyclodextrin works as a slow release system due to the complexation of adapalene with the bound cyclodextrin.

Example 16—Complexation of Adapalene

A solubility study was performed by adding excess amounts of adapalene (5 mg) to six glass vials containing 10 mL aqueous solutions of increasing concentrations of randomly methylated β-cyclodextrins (0-7×10⁻³ M) dissolved in 154 mM NaCl and 10 mM Na-phosphate (pH 7). The samples were mixed at room temperature for six days, and then they were centrifuged at 4000 rpm for 3 minutes. The supernatants were filtered through a 0.2 μm filter in order to remove undissolved adapalene. The UV absorbance of the filtrates was then measured at 320 nm in order to determine the concentration of dissolved adapalene. The concentration of adapalene in each sample was calculated from a calibration curve.

Figure 3:
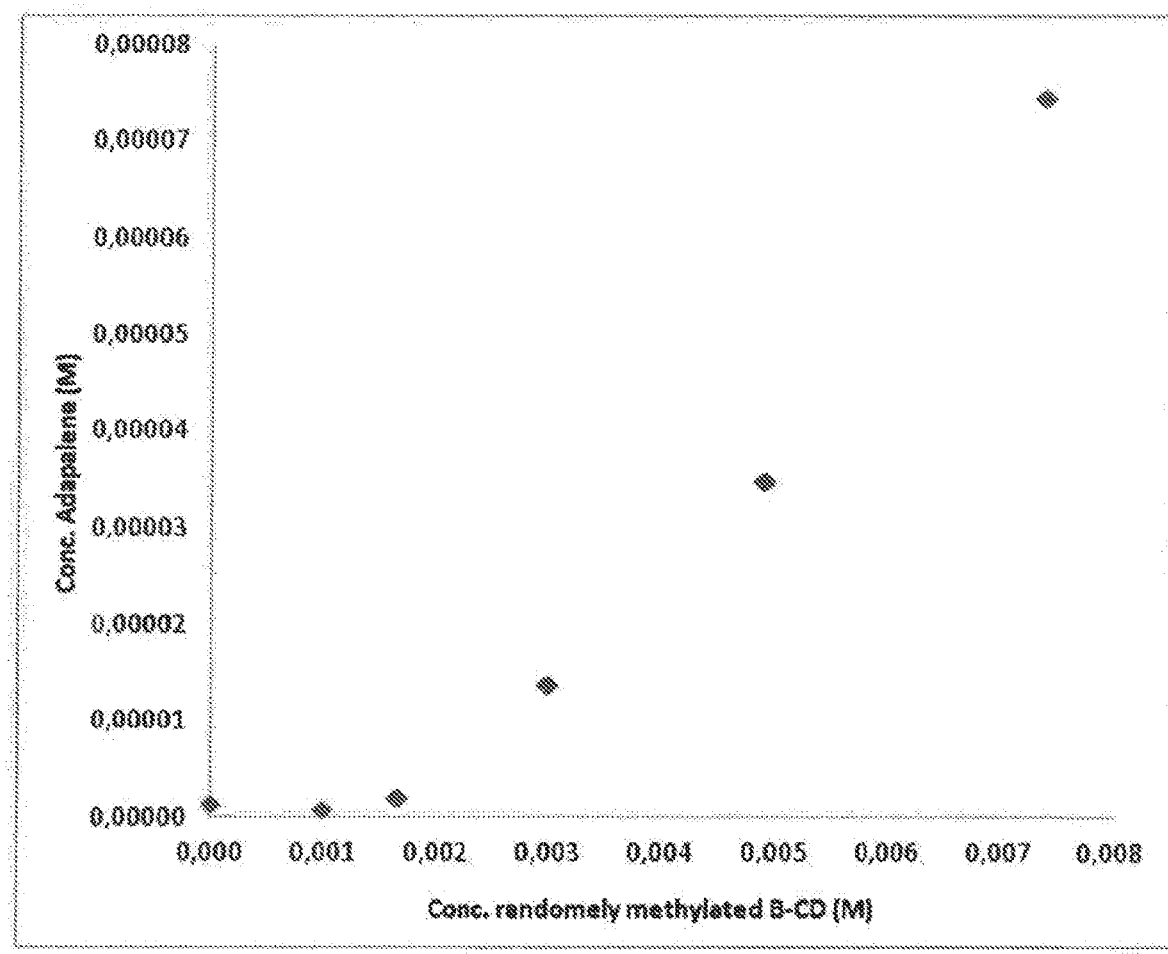
FIG. 3 shows solubility of adapalene in the presence of β-cyclodextrins.

The solubility graph in FIG. 3 shows that the solubility of adapalene increases with increasing CD concentration, proving complexation with β-cyclodextrins.

Example 17—NMR Analysis of Complexation Between Adapalene and Randomly Methylated β-Cyclodextrin Sample Preparation:

For sample 1, from the solubility diagram study in Example 16 containing 0.7 mM randomly methylated β-cyclodextrin and an excess of adapalene, 550 μl of the filtered sample, was added to a 2 ml Eppendorf tube. The sample was then lyophilized and the solvent exchanged to $D_2O$.

Sample 2 containing 1.5 mM randomly methylated β-cyclodextrin and 0.15 mM of adapalene dissolved in $D_2O$ and 1% DMSO-d6 was prepared by adding 550 μl of the sample to a 2 ml Eppendorf tube. The sample was then lyophilized and the solvent exchanged again to $D_2O$.

NMR Analysis:

For sample 1, 1D 1H single pulse, noesy presaturation and 2D ROESY experiments were run at 30 and 50° C. For sample 2, 1D 1H single pulse, noesy presaturation and 2D ROESY experiments were run at 50° C.

Figure 4:
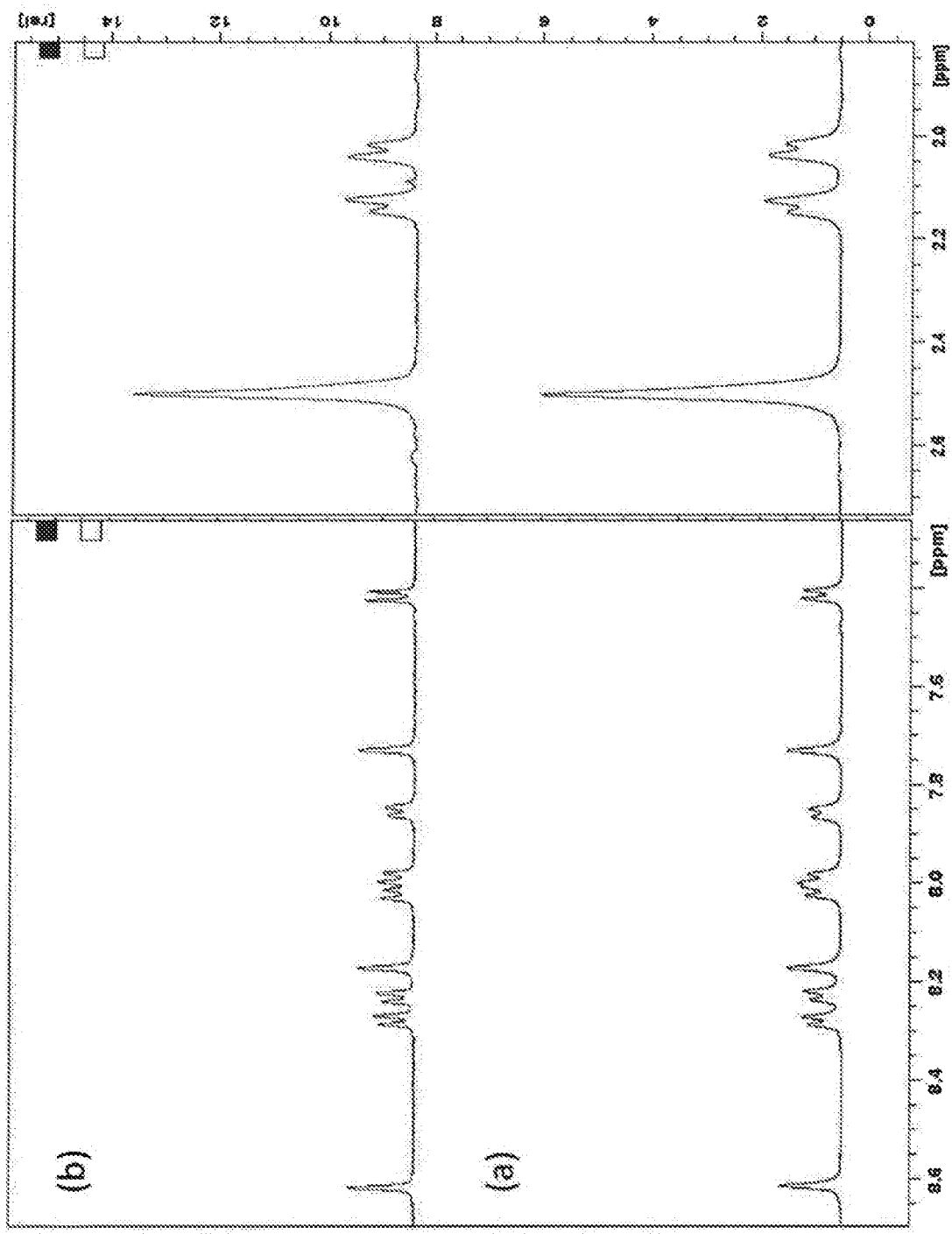
FIG. 4 shows NMR spectra of adapalene.

FIG. 4 shows 1D 1H NMR spectra of (a) sample 2 and (b) sample 1 showing similarity of adapalene chemical shifts.

The chemical shift is referenced to the HOD signal at 4.7 ppm. Signal intensity adjusted to equal heights for clarity.

The chemical shifts of the adapalene signals are close to identical in sample 1 and sample 2 1D 1H NMR spectra, see FIG. 4. That clearly indicates similar complexation in the two samples. Sample 2 has about 0.15 mM of complexed adapalene whereas sample 1 has about 0.075 mM complexed adapalene, according to solubility diagram data. NOE cross-peaks are observed between adapalene and randomly methylated β-cyclodextrin in sample 2 (data not shown). The existence of NOE cross-peaks between protons on adapalene and the inside of the cyclodextrin cavity is proof that adapalene is complexed with the cyclodextrin.

The invention claimed is:

1. A hyaluronic acid product comprising:
   (a) a cross-linked hyaluronic acid and one or more aminocyclodextrin host molecules, wherein the hyaluronic acid is cross-linked by ether bonds and wherein the one or more aminocyclodextrin host molecules are grafted onto the cross-linked hyaluronic acid by direct amide bonds between an amino group of the one or more aminocyclodextrin host molecules and a carboxyl group of the cross-linked hyaluronic acid; and
   (b) one or more guest molecules comprising 4-(2-((5,5,8,8-tetramethyl-5,6,7,8-tetrahydronaphthalen-2-yl)sulfonyl)ethyl)benzoic acid;
   wherein the one or more guest molecules form a guest-host complex with the one or more aminocyclodextrin host molecules.

2. The hyaluronic acid product according to claim 1, wherein the one or more aminocyclodextrin host molecules are constituted by 6-8 glucopyranoside units.

3. The hyaluronic acid product according to claim 2, wherein the one or more aminocyclodextrin host molecules are selected from the group consisting of 2 aminocyclodextrin, 3-aminocyclodextrin, and 6-aminocyclodextrin.

4. The hyaluronic acid product according to claim 1, wherein the one or more aminocyclodextrin host molecules and disaccharides of the cross-linked hyaluronic acid of the resulting hyaluronic acid product have a molar ratio of more than 2%.

5. The hyaluronic acid product according to claim 1, wherein the hyaluronic acid product is in the form of gel particles having an average size in the range of 0.01-5 mm.

6. A process of preparing a formulation of one or more guest molecules that form a guest-host complex with one or more aminocyclodextrin host molecules, the process comprising:
   (a) providing (i) hyaluronic acid and (ii) one or more aminocyclodextrin host molecules with the one or more guest molecules comprising 4-(2-((5,5,8,8-tetramethyl-5,6,7,8-tetrahydronaphthalen-2-yl)sulfonyl)ethyl)benzoic acid;
   (b) cross-linking the hyaluronic acid by ether bonds using a bi- or polyfunctional cross-linking agent;
   (c) grafting the one or more aminocyclodextrin host molecules onto the cross-linked hyaluronic acid by amide bonds; and
   (d) bringing a solution of the one or more guest molecules into contact with the one or more aminocyclodextrin host molecules grafted onto the cross-linked hyaluronic acid under conditions allowing for the formation of the guest-host complex between the one or more aminocyclodextrin host molecules and the one or more guest molecules, and optionally
   (e) recovering the guest-host complex bound to the cross-linked hyaluronic acid.

7. The process according to claim 6, wherein an amino group of the aminocyclodextrin molecule forms said amide bond with a carboxyl group of the cross-linked hyaluronic acid.

8. The process according to claim 6, wherein the grafting in (c) comprises:
   (i) activating the carboxyl groups on the cross-linked hyaluronic acid with a triazine-based coupling reagent to form an activated cross-linked hyaluronic acid, and
   (ii) coupling the one or more aminocyclodextrin molecules to the carboxyl groups of the activated cross-linked hyaluronic acid by amide bonds.

9. The process according to claim 6, wherein said bi- or polyfunctional cross-linking agent is selected from the group consisting of: 1,4-butanediol diglycidyl ether (BDDE), 1,2-bis(2,3-epoxypropoxy)ethylene (EGDGE), ethylene glycol diglycidyl ether (EGDE), 1,2-ethanediol diglycidyl ether (EDDE), and diepoxyoctane.

10. The process according to claim 6, further comprising providing particles of the hyaluronic acid product having an average size in the range of 0.01-5 mm.

11. A product obtainable by the process according to claim 6.

12. A method of cosmetically treating skin, the method comprising administering to the skin the hyaluronic acid product according to claim 1.

13. The hyaluronic acid product according to claim 5, wherein the hyaluronic acid product is in the form of gel particles having an average size in the range of 0.1-0.8 mm.

14. The hyaluronic acid product according to claim 1, wherein the one or more aminocyclodextrin host molecules comprise methyl groups or hydroxypropyl groups.

15. The hyaluronic acid product according to claim 1, wherein the one or more guest molecules are capable of being released from the guest-host complexes due to a change in pH that cleaves hydrogen or ionic bonds between the host and guest molecules.

16. The hyaluronic acid product according to claim 1, wherein the one or more guest molecules are capable of being released from the guest-host complexes due to enzymatic cleavage of α-1,4 linkages between glucose monomers.

17. The hyaluronic acid product according to claim 4, wherein the one or more aminocyclodextrin host molecules and disaccharides of the cross-linked hyaluronic acid of the resulting hyaluronic acid product have a molar ratio of more than 5%.

* * * * *